United States Patent [19]

Marion

[11] 4,081,253
[45] Mar. 28, 1978

[54] PRODUCTION OF PURIFIED SYNTHESIS GAS AND CARBON MONOXIDE

[75] Inventor: Charles P. Marion, Mamaroneck, N.Y.

[73] Assignee: Texaco Development Corporation, New York, N.Y.

[21] Appl. No.: 810,709

[22] Filed: Jun. 28, 1977

Related U.S. Application Data

[63] Continuation-in-part of Ser. No. 749,657, Dec. 10, 1976.

[51] Int. Cl.$^2$ .............................................. C10J 3/00
[52] U.S. Cl. .................... 48/197 R; 48/202; 48/215; 252/373; 260/449.5; 423/415 A
[58] Field of Search ............... 48/197 R, 202, 206, 48/212, 215; 252/373; 260/449.5; 423/415 A, 246, 248

[56] References Cited

U.S. PATENT DOCUMENTS

| | | | |
|---|---|---|---|
| 3,715,195 | 2/1973 | Tassoney et al. | 48/197 R |
| 3,920,717 | 11/1975 | Marion | 260/449.5 |

Primary Examiner—Robert L. Lindsay, Jr.
Assistant Examiner—George C. Yeung
Attorney, Agent, or Firm—Thomas H. Whaley; Carl G. Ries; Albert Brent

[57] ABSTRACT

A continuous process for simultaneously producing (1) a stream of purified synthesis gas having a controlled mole ratio $H_2/CO$, and (2) a separate stream of CO-rich gas. Methanol may be synthesized from the purified synthesis gas and reacted with CO to produce acetic acid. In the process, raw synthesis gas from a noncatalytic partial-oxidation gas generator is cleaned (if necessary), cooled, and dehumidified. At least a portion of the resulting gas stream is then partially purified by removing $H_2S$ and COS if present, and at least a portion of the $CO_2$ in a first gas purification zone. The remainder of the clean dehumidified gas stream if any, by-passes the first gas purification zone. Partially purified gas from the first gas purification zone is introduced into a second gas-purification or separation zone and at least a portion of the remainder if any, by-passes the second gas purification zone. A product stream of CO-rich gas and a separate stream of $H_2$-rich gas is removed from the second gas purification zone. The product stream of purified synthesis gas may then be produced by mixing together at least a portion of said $H_2$-rich gas stream with at least a portion of at least one of the following by-pass gas streams; (a) gas processed in the first gas purification zone that by-passes the second gas purification zone; (b) clean dehumidified gas that by-passes the first gas purification zone.

37 Claims, 2 Drawing Figures

PRODUCTION OF PURIFIED SYNTHESIS GAS AND CARBON MONOXIDE

CROSS-REFERENCE TO RELATED APPLICATION

This application is a continuation-in-part of my co-pending application, Ser. No. 749,657, filed Dec. 10, 1976.

BACKGROUND OF THE INVENTION

1. Field of the Invention

This is a partial-oxidation process in which synthesis gas having a controlled $H_2/CO$ mole ratio and either a CO-rich gas or substantially pure CO are simultaneously produced. Methanol may be made from the synthesis gas and then may be reacted with the CO-rich gas or with substantially pure CO to produce acetic acid.

2. Description of the Prior Art

Synthesis gas may be prepared by partial oxidation of a fossil fuel with a free-oxygen-containing gas, optionally in the presence of a temperature moderator. The effluent gas stream from the gas generator is cooled (below the temperature at which the gas composition approaches equilibrium) by, for example, direct immersion in water in a quench drum such as described in coassigned U.S. Pat. No. 2,896,927. By this method of gas cooling the sensible heat in the effluent gas stream is used to produce steam in the product gas.

Alternatively, the effluent gas stream from the gas generator may be cooled in a syngas cooler, such as shown in coassigned U.S. Pat. No. 3,920,717. By this method of gas cooling, the effluent gas stream does not become saturated with the water. In coassigned U.S. Pat. No. 3,929,429, in order to prepare an oil-carbon dispersion and a separate water-carbon dispersion which are simultaneously fed to a gas generator for producing fuel gas, a portion of the effluent gas stream is cooled in a syngas cooler and then scrubbed with oil; and another stream is quenched in water. Noncatalytic thermal shift is used to adjust the $H_2/CO$ mole ratio of a single stream of synthesis gas in coassigned U.S. Pat. No. 3,920,717.

SUMMARY

In the subject process, the effluent gas stream directly from a free-flow unpacked noncatalytic partial-oxidation synthesis gas generator may have an $H_2/CO$ mole ratio in the range of about 0.5 to 1.9 and may contain entrained particulate solids, i.e. ash and carbon soot. A portion of the ash if present, may first be removed as slag. The gas stream is then cooled by indirect heat exchange in a gas cooler, and boiler-feed water is thereby converted into steam. Any remaining entrained solids, i.e. particulate carbon are then removed. The soot-free gas stream is dehumidified and then at least a portion of the soot-free and dehumidified gas stream is introduced into a first gas-purification zone. The remainder of the soot-free and dehumidified gas stream if any, by-passes the first gas-purification zone. In the first gas purification zone, depending on the composition of the soot-free and humidified gas stream any $H_2S$, COS, and at least a portion of the $CO_2$ is removed by conventional procedures. This may be done in one or two stages. Gas which has been processed in the first gas purification zone is introduced into a second gas purification or separation zone whereby conventional procedures a product stream of CO-rich gas and a separate stream of $H_2$-rich gas, and optionally $CH_4$-rich gas are separated. For example, at least a portion of the gas from the first gas purification zone containing no $H_2S$ and COS and with at least a portion of the $CO_2$ removed is passed into the second gas purification zone. The remainder of the gas which has been processed in the first gas purification zone if any, by-passes the second gas purification zone. The product stream of purified synthesis gas having a controlled $H_2/CO$ mole ratio i.e. in the range of about 2 to 12 is produced by mixing together at least a portion of the $H_2$-rich gas from the second gas purification zone with at least one i.e. either one or both of the following: (a) gas processed in the first gas purification zone that by-passes the second gas purification zone if any; and (b) soot-free dehumidified gas stream that by-passes the first gas-purification zone if any. For example: In one embodiment where the soot-free and dehumidified synthesis gas stream is substantially free-from $H_2S$ and COS, then $H_2$-rich gas may be mixed with at least a portion of at least one of the following: (a) soot-free and dehumidified gas that by-passes the first gas-purification zone; (b) soot-free and dehumidified gas having at least a portion of the $CO_2$ removed from the first gas purification zone that by-passes the second gas-purification zone.

In another embodiment where the soot-free and dehumidified gas stream contains $H_2S$ and COS then the $H_2$-rich gas may be mixed with at least a portion of at least one i.e. either one or both of the following: (a) desulfurized gas from the first stage of the first gas purification zone; (b) desulfurized gas with at least a portion of the $CO_2$ removed from the second stage of the first gas purification zone that by passes the second gas purification zone.

The step of catalytic water-gas shift reaction is not a required step in the subject process. Optionally, thermal noncatalytic shift may be employed to increase the $H_2/CO$ mole ratio of the raw effluent gas stream from the gas generator.

In another embodiment, methanol synthesis gas having a mole ratio $H_2/CO$ in the range of about 2 to 4 is produced by the aforesaid process and catalytically converted into a stream of raw methanol. Pure methanol is obtained by purifying this stream. A portion of the pure methanol may be used as a solvent absorbent to remove acid gases from the raw synthesis gas in the first gas-purification zone. Optionally, at least a portion of the pure methanol may be catalytically reacted with at least a portion of said product stream of substantially pure carbon monoxide to produce a stream of crude acetic acid, which may be purified to produce glacial acetic acid and by-product oxygen-containing materials. The by-product oxygen-containing materials may be recycled to the reaction zone of the gas generator.

BRIEF DESCRIPTION OF THE DRAWING

The invention will be further understood by reference to the accompanying drawing.

FIG. IB as shown to the right of line A—A is a schematic representation of another embodiment of the process, in which pure methanol is produced from a product stream of methanol synthesis gas made by the subject process. Optionally, at least a portion of said pure methanol may be then reacted with at least a portion of the substantially pure carbon monoxide stream to produce acetic acid.

DESCRIPTION OF THE INVENTION

In the first step of the subject process, raw synthesis gas, substantially comprising hydrogen and carbon monoxide and having a mole ratio ($H_2/CO$) in the range of about 0.5 to 1.9, is produced by partial oxidation of a hydrocarbonaceous fuel with substantially pure oxygen, optionally in the presence of a temperature moderator in the reaction zone of an unpacked free-flow noncatalytic partial-oxidation gas generator. The stream-to-fuel weight ratio in the reaction zone is in the range of about 0.1 to 5, and preferably about 0.2 to 0.7. The atomic ratio of free-oxygen to carbon in the fuel (O/C ratio), is in the range of about 0.6 to 1.6, and preferably about 0.8 to 1.4. The reaction time is in the range of about 1 to 10 seconds, and preferably about 2 to 6 seconds.

The raw synthesis gas stream exits from the reaction zone at a temperature in the range of about 1300° to 3000° F., such as 1600° to 3000° F, say 2000° to 2800° F and at a pressure in the range of about 1 to 250 atmospheres (atm.), such as 10 to 200 atm. say 40 to 150 atm.

The composition of the raw synthesis gas leaving the gas generator is about as follows, in mole percent: $H_2$ 60 to 29, CO 30 to 60, $CO_2$ 2 to 25, $H_2O$ 2 to 20, $CH_4$ nil to 25, $H_2S$ nil to 2, COS nil to 0.1, $N_2$ nil to 1, and $A_r$ nil to 0.5. There may also be present particulate carbon in the range of nil to 20 weight % (basis carbon content in the original feed), and ash in the amount of nil to 60 weight % of the original hydrocarbonaceous feed.

The synthesis gas generator comprises a vertical cylindrically shaped steel pressure vessel lined with refractory, such as shown in coassigned U.S. Pat. No. 2,809,104. A typical quench drum is also shown in said patent. A burner, such as shown in coassigned U.S. Pat. No. 2,928,460, may be used to introduce the feed streams into the reaction zone.

A wide range of combustible carbon-containing organic materials may be reacted in the gas generator with a free-oxygen containing gas, optionally in the presence of a temperature-moderating gas, to produce the synthesis gas.

The term hydrocarbonaceous as used herein to describe various suitable feedstocks is intended to include gaseous, liquid, and solid hydrocarbons, carbonaceous materials, and mixtures thereof. In fact, substantially any combustible carbon-containing organic material, or slurries thereof, may be included within the definition of the term "hydrocarbonaceous." For example, there are (1) pumpable slurries of solid carbonaceous fuels, such as coal, particulate carbon, petroleum coke, concentrated sewer sludge, and mixtures thereof, in a vaporizable liquid carrier, such as water, liquid hydrocarbon fuel, and mixtures thereof; (2) gas-solid suspensions such as finely ground solid carbonaceous fuels dispersed in either a temperature-moderating gas or in a gaseous hydrocarbon; and (3) gas-liquid-solid dispersions, such as atomized liquid hydrocarbon fuel or water and particulate carbon dispersed in a temperature moderating gas. The hydrocarbonaceous fuel may have a sulfur content in the range of about 0 to 10 wt. percent and an ash content in the range of about 0 to 60 wt. percent. By definition, the term "substantially sulfur-free hydrocarbonaceous fuel" as used herein shall be a hydrocarbonaceous fuel as previously described which when subjected to the noncatalytic partial oxidation process will produce raw synthesis gas, in the manner previously described, containing less than 5 parts per million (PPM) of $H_2S$ and COS.

The term liquid hydrocarbon, as used herein to describe suitable liquid feedstocks, is intended to include various materials, such as liquefied petroleum, liquefied natural gas, petroleum distillates and residua, gasoline, naphtha, kerosine, crude petroleum, asphalt, gas oil, residual oil, tar-sand oil and shale oil, coal derived oil, aromatic hydrocarbons (such as benzene, toluene, xylene fractions), coal tar, cycle gas oil from fluid-catalytic-cracking operations, furfural extract of coker gas oil, and mixtures thereof.

Gaseous hydrocarbon fuels, as used herein to describe suitable gaseous feedstocks, include methane, ethane, propane, butane and other unsaturated light hydrocarbon gases, pentane, natural gas, water-gas, coke-oven gas, refinery gas, acetylene tail gas, ethylene off-gas, synthesis gas, and mixtures thereof. Solid, gaseous, and liquid feeds may be mixed and used simultaneously; and these may include paraffinic, olefinic, acetylenic, naphthenic, and aromatic compounds in any proportion.

Also included within the definition of the term hydrocarbonaceous are oxygenated hydrocarbonaceous organic materials including carbohydrates, cellulosic materials, aldehydes, organic acids, alcohols, ketones, oxygenated fuel oil, waste liquids and by-products from chemical processes containing oxygenated hydrocarbonaceous organic materials, and mixtures thereof.

The hydrocarbonaceous feed may be at room temperature, or it may be preheated to a temperature up to as high as about 600° to 1200° F. but preferably below its cracking temperature. The hydrocarbonaceous feed may be introduced into the gas-generator burner in liquid phase or in a vaporized mixture with the temperature moderator.

The need for a temperature moderator to control the temperature in the reaction zone depends in general on the carbon-to-hydrogen ration of the feedstock and the oxygen content of the oxidant stream. A temperature moderator may not be required with some gaseous hydrocarbon fuels; however, generally one is used with liquid hydrocarbon fuels and with substantially pure oxygen. Steam may be introduced as the preferred temperature moderator in admixture with either or both reactant streams. Alternatively, the temperature moderator may be introduced into the reaction zone of the gas generator by way of a separate conduit in the burner. Other suitable temperature moderators may include $CO_2$ and a portion of cooled and recycled synthesis gas separated downstream in the process.

The term free-oxygen-containing gas as used herein means substantially pure oxygen, i.e. greater than about 95 mole % oxygen (the remainder usually comprising $N_2$ and rare gases). Free-oxygen-containing gas may be introduced by way of the partial-oxidation burner at a temperature in the range of about ambient to 1800° F.

A continuous stream of hot effluent gas, at substantially the same temperature and pressure as in the reaction zone leaves from the axial exit port of the gas generator and is cooled in a gas cooler. However, for hydrocarbonaceous fuels containing a high ash content such as coal, a solids separation zone is preferably inserted between the exit port of the gas generator and said gas cooler in order to remove the larger entrained solid particles. This solids separation zone may comprise a catch-pot, slag chamber, cyclone separator, electrostatic precipitator, or combinations of such schemes for removing at least a portion of any solid matter i.e particulate carbon, ash, metal constituents, scale, slag, refractory, and mixtures thereof that may be entrained in the hot effluent gas stream, or which may flow from the gas generator i.e. slag, ash, bits of refractory. Thus, a portion of the larger solid particles, if present may be separated from the effluent gas stream and recovered with very little, if any temperature or pressure drop in the process gas stream. A typical slag chamber that may be employed is shown in the drawing, or in FIG. 1 of the drawing for coassigned U.S. Pat. No. 3,528,930. Any coarse solid particles above the size of about 12 microns are preferably removed at this time by means of gravity or cyclone separation or other physical cleaning process. If particulate carbon soot is entrained in the effluent gas stream, a small amount may be removed with the coarser particles. However, most of the soot and finer entrained solids are removed subsequently by scrubbing the process gas stream with water. In the preferred embodiment, the step of water-gas shift reaction to increase the $H_2/CO$ mole ratio is not required. This will eliminate costly water-gas shift catalysts. Optionally, in a separate embodiment, noncatalytic thermal shifting, as described in coassigned U.S. Pat. No. 3,723,345 may be employed.

In such case, the stream of hot effluent gas leaving the gas generator is passed into a separate refractory lined free-flow reaction chamber where some of the entrained solids are removed and adjustment of the mole ratio ($H_2/CO$) is effected. Preferably the process gas stream is at a temperature in the range of about 1600° to 3500° F as produced in the gas generator and at the same pressure as in the gas generator e.g. 15 to 200 atmospheres such as 60 to 150 atmospheres. A chamber as shown in coassigned U.S. Pat. No. 3,565,588 may be used. For example, spherical chamber 37 as shown in the drawing is unpacked and free from catalyst or obstruction to the flow of gas therethrough. A portion of the solid matter that may be entrained in the process gas stream may drop out and may be removed through an outlet located at the bottom of the spherical chamber which leads to a lock hopper.

A stream of supplemental $H_2O$ i.e. stream as produced subsequently in the process is simultaneously introduced into the spherical chamber at a temperature in the range of about 500° to 1500° F and at a pressure slightly above that in the gas generator. On a dry basis, about 0.1 to 2.5 moles of supplemental $H_2O$ are preferably introduced into the spherical chamber per mole of effluent synthesis gas from the gas generator, where the gases mix. Alternatively, the supplemental $H_2O$ may be introduced into the separate noncatalytic unobstructed thermal shift conversion zone in admixture with the effluent synthesis gas from the gas generator. By noncatalytic thermal direct water-gas shift reaction at a temperature of at least 1500° F and preferably in the range of about 1700° F to 2800° F, the supplemental $H_2O$ reacts with a portion of the carbon monoxide in the effluent synthesis gas stream from the generator so as to produce additional $H_2$ and $CO_2$. The mole ratio ($H_2/CO$) of the effluent stream of gases from the gas generator may be increased by this step to a value in the range of about 0.8 to 6, such as 2.0 to 4.0. The aforesaid high temperature adiabatic noncatalytic thermal direct water-gas shift reaction begin for example in the insulated spherical chamber. The shift reaction may continue in an insulated line connecting the side outlet of the spherical chamber with the bottom flanged inlet to a gas cooler. Thus, the effluent stream of synthesis gas is thermally shifted without a catalyst in transit between stages in the process. Residence time in the water gas shift conversion zone is in the range of about 0.1 to 5 seconds. Preferably, the condition of temperature and presure at which the noncataytic thermal direct water-gas shift reaction takes place are substantially the same as those in the synthesis gas generator, less ordinary line drop and less any cooling due to the sensible heat of the supplemental $H_2O$ and any heating due to the heat of reaction.

Next, the process gas stream is passed through an inline separate gas cooler in noncontact heat exchange with water. The stream of synthesis gas is cooled to a temperature in the range of about 350° to 750° F. By-product saturated steam may be produced thereby at a pressure above the pressure of the synthesis gas for use elsewhere in the process. Substantially all of the steam requirement in the system may be therefore met. For example, the aforesaid steam may be used as a working fluid in an expansion turbine for the production of power. The steam turbine may be used to drive the air and oxygen compressors in a conventional air separation unit, the recycle gas compressor in the methanol synthesis loop to be further described, or the feed gas compressor if any. Preferably, a portion of the steam may be introduced into the gas generator as at least a portion of the temperature moderator and into the thermal shift reactor as a reactant. It may also be used to provide heat in a reboiler in a methanol or DME distillation column.

The stream of synthesis gas leaving the waste heat boiler may be passed through a gas cleaning zone where any remaining entrained solid particles if present, are removed.

When there is substantially no entrained particulate matter in the process gas stream, such as with some gaseous feedstocks, both gas cleaning zones may be by-passed or eliminated. The amount of solid particles i.e., selected from the group: particulate carbon, ash, and mixtures thereof, that may be entrained in the synthesis gas is dependent on the type of hydrocarbonaceous fuel and the atomic ratio (O/C) in the reaction zone. When the generator fuel contains metals i.e. nickel and vanadium compounds, a small amount of entrained particulate carbon i.e., about 1–2 wt. % (basis weight of C in the hydrocarbonaceous feed), will increase the life of the refractory lining the gas generator.

Any suitable means may be used for cleaning entrained solid particles from the process gas streams. For example the gas stream leaving the gas cooler may be contacted with a scrubbing fluid, such as water or liquid hydrocarbon in one or more steps in a gas-scrubbing zone, such as shown in coassigned U.S. Pat. No. 3,544,291. The solids dispersed in scrubbing fluid from the gas cleaning zone, may be returned to the gas generator as at least a portion of the feed. Thus, if the gas stream is scrubbed with water, the dispersion of particulate carbon and water which is formed may be concentrated or separated by conventional means to yield clarified water. This water may be recycled to an orifice, nozzle, or venturi scrubber in the gas cleaning zone. Carbon concentration may be effected by any suitable means; e.g., filtration, centrifuge, gravity settling, or by well-known liquid hydrocarbon extraction, such as the process described in coassigned U.S. Pat. No. 2,992,906.

The gas stream leaving the cleaning zone is cooled below the dew point by indirect i.e. noncontact heat exchange and then introduced into a knockout or separation vessel in which substantially all of the water is removed to produce a clean i.e. soot-free dehumidified gas stream.

When the $H_2S$ and COS content of the soot-free dehumidified gas stream is less than about 5 PPM (parts per million), then the gas stream does not have to be desulfurized. In such case, the first gas purification zone is used only to remove at least a portion i.e. about 10 to 100 vol. % of the $CO_2$ present. Thus, about 10 to 100 vol. %, such as 10 to 90 vol. % of the clean dehumidified gas from the partial oxidation gas generator may be introduced into the first gas purification zone. The remainder of the soot-free dehumidified gas stream if any by-passes the first purification zone. The $CO_2$-rich gas stream removed in the first gas purification zone may comprise the following in mole %: $CO_2$ 40 to 100, $H_2$ 5 to 25, CO 10 to 40, and $CH_4$ nil to 5.

When a portion i.e. (about 10–90 vol %) of the soot-free dehumidified synthesis gas by-passes the first gas purification zone then, at least a portion i.e. about 10 to 100 vol. % of the gas stream leaving the first gas purification zone with at least a portion of the $CO_2$ removed is passed into a second gas purification zone. The remainder of the gas stream from the first gas purification zone if any, by-passes the second gas purification zone. When no soot-free dehumidified synthesis gas by-passes the first gas purification zone then a portion i.e. about 10 to 90 vol. % of the gas stream leaving the first gas purification zone is passed into the second gas purification zone, and the remainder i.e. about 90 to 10 vol. % by-passes the second gas purification zone. Thus, in this embodiment there is always at least one gas stream that by-passes the first, second, or both gas purification zones, and which may be mixed with $H_2$-rich gas stream produced in the second gas purification zone to produce the product synthesis gas.

A CO-rich product gas stream and a $H_2$-rich gas stream are separated in said second gas purification or separation zone. The composition of the CO-rich gas stream produced in the second gas purification zone is about as follows in mole % : CO 61 to 99; N nil to 1; $CO_2$ nil to 15; $H_2$ 2 to 8; $CH_4$ nil to 1; and Ar nil to 0.5. Preferably by further purification, substantially pure carbon monoxide (90–99.5 mole % CO) may be produced. The $H_2$-rich gas stream produced in the second purification zone may comprise in mole % : $H_2$ 98 to 60; CO nil to 5; $CO_2$ nil to 5; $CH_4$ nil to 5; Ar nil to 4; and $N_2$ nil to 20.

From about 20 to 100 vol. %, and preferably all of the $H_2$-rich gas stream may be included as one of the ingredients in the product gas. The remainder of the $H_2$-rich gas stream may be exported.

When the soot-free dehumidified process gas stream contains substantially no $H_2S$ and COS, the product gas stream of purified synthesis gas is made by mixing at least a portion i.e. about 10 to 100 vol. % of said $H_2$-rich gas stream with at least a portion i.e. about 10 to 100 vol. % of at least one of the following by-pass gas streams: (a) soot-free dehumidified gas that by-passes the first gas purification zone; (b) soot-free dehumidified gas with at least a portion of the $CO_2$ removed that leaves the first gas purification zone and which by-passes the second gas purification zone. Mixtures of (a) and (b) may include about 10 to 90 vol. % of (a) and the remainder (b).

In another embodiment, more than 5 PPM of acid gases i.e. $H_2S$, COS, and $CO_2$ are found in the soot-free dehumidified gas stream. In such case, all of this gas stream is introduced into a first gas purification zone which comprises a first-stage for desulfurizing the process gas streams and a second-stage for removing at least a portion i.e. about 10 to 100 volume % of the desulfurized gas stream from the first stage is introduced into the second stage where at least a portion of the $CO_2$ contained therein is removed. The remainder of the desulfurized gas stream by-passes said second stage and the second gas purification zone. One or more liquid solvent absorbents may be used in the two-stages to absorb the acid-gas impurities. The rich liquid solvent absorbent is then removed from the absorption tower and regenerated by heating, stripping, or flashing, or a combination thereof to produce a lean liquid solvent absorbent which is then recycled to the conventional gas absorption tower. The acid-gases are recovered during the regeneration of the solvent absorbent and may be sent to a Claus unit for the production of sulfur. When a portion of the desulfurized gas stream from the first stage by-passes the second i.e $CO_2$-absorption stage of the first gas purification zone and the second gas purification zone then at least a portion i.e. about 10 to 100 vol. % of the desulfurized gas stream leaving the second stage of the first gas purification zone is introduced into a second gas purification zone where a $H_2$-rich gas stream and a CO-rich product gas stream are separated. The remainder of the gas stream leaving the second stage of the first gas purification zone if any, by-passes said second gas purification zone. Alternately, when all of the desulfurized gas stream from the first stage is introduced into the second stage of the first gas purification zone, then a portion i.e. about 10 to 90 vol. % of the desulfurized gas stream with at least a portion of the $CO_2$ removed from the first gas purification zone is introduced into the second gas purification zone. The remainder i.e. about 90 to 10 vol. % of the gas stream leaving the second stage of the first gas purification zone by-passes the second gas purification zone. Thus, in this embodiment there is always at least one gas stream that by-passes the second gas purification zone which may be mixed with the $H_2$-rich gas stream to produce the purified synthesis gas product. As previously mentioned, the $H_2$-rich gas is produced in the second gas purification zone along with a CO-rich product stream.

The product stream of purified synthesis gas having a controlled mole ratio $H_2$/CO is produced in this embodiment by the following manner. At least a portion i.e. about 10 to 100 vol. % of the $H_2$-rich gas from the second purification zone is mixed with at least a portion i.e. about 10 to 100 vol. % of at least one i.e. either one or both of the following gas streams: (a) desulfurized gas stream from the first stage that by-passes the $CO_2$-removal stage of the first gas purification zone; (b) desulfurized gas stream with at least a portion i.e. about 10 to 100 vol. % of the $CO_2$ removed that leaves the second stage of said first gas purification zone and by-passes said second gas purification zone. Mixtures of (a) and (b) may comprise about 10–90 vol. % of (a) and the remainder (b).

Alternately, a liquid solvent absorbent may be employed which absorbs all of the $H_2S$ and COS and at least a portion of the $CO_2$ in a single stage absorption tower which constitutes the first gas purification zone. In such case all of the clean soot-free dehumidified gas stream is passed into the first gas purification zone and a portion i.e. about 10 to 90 vol. % of the desulfurized gas with at least a portion i.e. 10 to 100 vol. % of the $CO_2$ removed from the first gas purificatiofn zone is introduced into the second gas purification zone, while the remainder of this gas stream by-passes the second gas purification zone. A CO-rich product gas stream and a $H_2$-rich gas stream are separated in the second gas purification zone. The purified synthesis gas product stream is produced by mixing together at least a portion i.e. 10 to 100 vol. % of said $H_2$-rich gas stream and at least a portion i.e. about 10-100 vol. % of the desulfurized gas with at least a portion i.e. 10 to 100 vol. % of the $CO_2$ removed that by-passes the second gas purification zone.

Any suitable conventional process may be used for purifying the gas stream in the first gas purificaton zone. Typical gas purification processes may involve refrigeration and physical or chemical absorption with a solvent, such as methanol, N-methyl-pyrrolidone, triethanolamine, propylene carbonate, or alternatively with hot potassium carbonate.

Advantageously, when methanol is used as the solvent, a portion of the product methanol may be used as make-up to the gas-purification zone. By scrubbing the synthesis gas with methanol at 0° C and 10 atmospheres 100 volumes of $CO_2$ are absorbed per volume of methanol. This concentration is increased to 270 vol/vol at − 30° C. At a high partial pressure of $CO_2$ e.g. 250 psi. methanol offers a very high absorption power. Similarly, cold methanol is an excellent selective solvent for separating $H_2S$ and COS from $CO_2$. For example, the gas stream may be washed with cold methanol and the total sulfur, $H_2S$ + COS, may be reduced to less than 0.1 ppm. By selective absorption of $H_2S$ and COS a concentration of high sulfur in the off-gas is obtained that contributes toward economic sulfur recovery.

In physical absorption processes, most of the $CO_2$ absorbed in the solvent may be released by simple flashing. The rest may be removed by stripping. This may be done most economically with nitrogen. Nitrogen may be available as a low cost by-product when a conventional air separation unit is used for producing substantially pure oxygen (95 mole % $O_2$ or more) for use as the free-oxygen containing gas in the synthesis gas generator. Optionally, a portion of the $CO_2$ separated in the first gas purification zone may be recycled to the gas generator. The regenerated solvent is then recycled to the absorption column for reuse. When necessary, final cleanup may be accomplished by passing the gas stream through iron oxide, zinc oxide, or activated carbon to remove residual traces of $H_2S$ or organic sulfur. Similarly, the $H_2S$ and COS-containing solvent may be regenerated by flashing or by stripping with nitrogen or, alternatively, by heating and refluxing at reduced pressure without using an inert gas. The $H_2S$ and COS may be then converted into sulfur by a suitable process. For example, the Claus process may be used for producing elemental sulfur from $H_2S$, as described in Kirk-Othmer Encyclopedia of Chemical Technology, Second Edition Volume 19, John Wiley, 1969, Page 352. Excess $SO_2$ may be removed and discarded in chemical combination with limestone, or by means of a suitable commercial extraction process.

In an alternate gas purification scheme employing autorefrigeration, from about 30 to 95% of the carbon dioxide may be removed from the synthesis gas stream, along with substantially all of the $H_2S$, in the first gas purification zone. For example, reference is made to coassigned U.S. Pat. No. 3,614,872 in which a stream of shifted synthesis gas is separated into an enriched hydrogen stream and an enriched carbon-dioxide stream by counter-current cooling with a departing stream of liquid $CO_2$ which is expanded and vaporized to produce low temperature.

The partially purified synthesis gas stream leaves the first gas purification zone at a temperature of the range of about −80° to 250° F and at a pressure in the range of about 10 to 450 atmospheres (preferably substantially equal to the pressure in the reaction zone of the synthesis gas generator, less ordinary line drop). The composition of this partially purified stream of synthesis gas is about as follows in mole %: $H_2$ 70 to 30, CO 30 to 60, $CO_2$ nil to 15, $H_2O$ nil to 2, $CH_4$ nil to 2, Ar nil to 2, $N_2$ nil to 15, $H_2S$ nil, and COS nil.

The aforesaid stream of partially purified synthesis gas may be split into two streams, depending upon the amount and composition of the carbon monoixide-rich gas required and the desired composition of the product stream of synthesis gas. The split may be pre-determined by material balances. Thus from about 10 to 100 vol. %, such as 10 to 90 vol. % of the stream of cleaned and partially purified synthesis gas leaving the first gas purification zone may be introduced into a second gas purification zone.

The second gas purification or separation zone may comprise any suitable conventional process for separating out a CO-rich gas, a $H_2$-rich gas stream, and optionally a $CH_4$-rich gas stream. Cryogenic cooling or physical absorption with a liquid solvent e.g. copper ammonium acetate or cuprous aluminum chloride, liquid nitrogen, and liquid methane may be employed.

One system for removing CO from the gas stream by physical absorption in cold copper liquor in a CO-absorption column will be described below. Upon applying heat and releasing the pressure on the copper liquor in a copper-liquor regeneration column, a relatively pure carbon monoxide is obtained. The reaction is shown in Equation I.

$$Cu_2(NH_3)_4^{++} + 2CO + 2NH_3^{++} \rightarrow Cu_2(NH_4)_6(CO)_2^{++} \qquad (I)$$

Thus, in the second gas purification zone at least a portion of the effluent gas stream from the first gas purification zone may be contacted in a conventional packed or tray-type column with a countercurrent flowing stream of, for example, cuprous acetate dissolved in aqua-ammonia solution. The temperature is preferably in the range of about 32° to 100° F and the pressure is preferably in the range of about 50 to 600 atm. Preferably, the pressure in the CO separation zone is substantially the same as that in the gas generator, less ordinary pressure drop in the lines and equipment. By keeping the pressure in the gas generator high enough, a gas compressor may be avoided between the acid-gas-absorption column in the first gas purification zone and the CO-absorption column in the second gas purification zone. Advantageously, the product stream of purified synthesis gas may be delivered at a pressure which is about that in the partial oxidation gas generator less ordinary drop in the intervening lines and equipment.

A typical analysis (by weight %) of the copper-liquor solution may include the following: $Cu^+$ 10; $Cu^{++}$ 2.2;

$CO_3^-$ (carbonate) 13.9; $HCO_3^-$ (bicarbonate) 1.3; and $NH_4^+$ 16.5. The acid radical in the aqueous solution may be either carbonate, formate, or acetate.

Regeneration of the copper liquor and release of the CO-rich gas stream takes place in a copper-liquor regenerator. The pressure difference between the scrubber and the regenerator is about 68 to 204 atm. e.g. 109 atm. By the reduction of pressure and the addition of heat and a free-oxygen containing gas, e.g. air, pure $O_2$, and mixtures thereof, the direction of Equation I may be reversed and the carbonate and bicarbonate ions may be regenerated. The normal temperature range in the regenerator may be about 170° to 180° F. Fresh make-up ammonia and, for example, acetic acid may be added to the copper liquor in the regenerator in order to maintain the proper solution chemistry. Optionally, the acetic acid may be produced subsequently in one embodiment of the subject process. In one separation process, the partially purified synthesis gas stream from the first gas purification zone is contacted with liquid methane or a sulfur-free liquefied $CH_4$-rich gas comprising at least 85 vol. % $CH_4$, such as liquid natural gas in a separation column. The bottoms stream from the column may then be passed into the partial oxidation gas generation operation as at least a portion of the feed.

In one embodiment of the subject invention, clean purified methanol synthesis gas is produced having a mole ratio $H_2/CO$ in the range of about 2 to 4 by the previously described process steps. By conventional catalytic steps the synthesis gas may be converted into methanol.

The equilibrium exothermic reaction of carbon oxides and oxygen to produce methanol, as shown in Equations II and III below, is favored by low temperature and high pressure. However, elevated temperatures may be necessary with some catalysts to obtain commercially adequate reaction rates.

$$CO + 2H_2 \rightarrow CH_3OH \qquad \qquad II$$

$$CO_2 + 3H_2 \rightarrow CH_3OH \qquad \qquad III$$

Conventional high-pressure measure processes operate at temperatures in the range of about 650° to 750° F, at pressures in the range of about 250 to 350 atm. and Conventional low- and intermediate-pressure methanol processes operate at temperatures in the range of about 400° to 660° F., such as 440°–520° F.; at pressures in the range of about 40 to 250 atm., such as 40 to 150, and with catalysts composed largely of copper oxide with a lesser amount of zinc oxide and either chrome or aluminum oxides. The proportions of these three oxides are 30 to 60%, 20 to 40%, and 5 to 20%, respectively. Durability and thermal stability of the catalyst may be improved by the addition of manganese or vanadium. Methanol catalysts may be prepared by alkaline precipitation from nitric-acid solution, followed by drying, calcining, and pelletizing. Space velocities may range from about 10,000 to 40,000 $hr^{-1}$. Contact times are below 1.0 second. This rate of methanol formation is from about 0.3 to 2.0 kg/liter of catalyst/hr.

Optionally, the gaseous feed to the methanol converter may contain about 2 to 12 mole % of $CO_2$. Also, the mole ratio, $H_2/(2CO+3CO_2)$, in the feed gas stream to the methanol converter may be in the range of about 1.01 to 1.05. The presence of some $CO_2$ reduces the cost of the prior gas purification step. Further, the greater molar specific heat of the $CO_2$ relative to CO and the lower heat of reaction of the $CO_2$ provide a more uniform temperature control in the methanol reactor. The presence of $CO_2$ appears to be beneficial in repressing the formation of dimethyl ether. Optionally, $CO_2$ obtained from said first gas purification zone may be mixed with the methanol synthesis gas to adjust the mole % of $CO_2$ present.

Each mole of fresh methanol synthesis gas may be mixed with 0 to 10 moles of unconverted recycle gas from the methanol converter, i.e. 3 to 8 moles of recycle gas per mole of fresh methanol synthesis gas. A steam-turbine-driven circulating compressor may be used to compress and to circulate a mixture comprising the fresh methanol synthesis gas and the recycle gas. The working fluid for the turbine, i.e. steam, may be obtained from the main syngas cooler following the gas generator.

The feed-gas mixture to the methanol converter is preferably preheated by indirect heat exchange with the gaseous effluent stream departing from the methanol converter at a temperature in the range of about 500° to 800° F and at a pressure in the range of about 20 to 450 atm., preferably at the pressure in the synthesis gas generator less ordinary drop in the intervening lines and equipment. The effluent stream from the methanol reactor may have the following principal ingredients, in mole %: $CH_3OH$ 5 to 15; CO 8 to 25; $H_2$ 40 to 80; $CO_2$ 3 to 12; $H_2O$ 0.5 to 15; and $(CH_3)_2O$ 0.05 to 0.6. Minor amounts of other alcohols, aldehydes, and ketones may be present.

Further cooling of the effluent gas stream in air and water coolers may be effected to condense crude methanol and water. This condensate flows to a separation zone in which uncondensed unreacted gases, i.e. $H_2$, $CO_2$, $CH_4$, $N_2$, A, are separated, for example by flashing, and recycled to the gas compressor, with the exception of any purge stream. The crude methanol is purified by fractional distillation. Impurities including low-boiling compounds, principally dimethyl ether and higher alcohols, may be withdrawn from the distillation zone and optionally may be disposed as a waste stream or be used by recycling to the gas generator as a portion of the feed. Advantageously, these waste streams contain combined oxygen and therefore reduce the free-oxygen gas required for a given level of soot production. A portion of the product methanol may be introduced into one or both gas-purification zones in the first and second trains, as make-up solvent absorbent.

In the following embodiment of the subject invention, first methanol synthesis gas having a mole ratio $H_2/CO$ in the range of about 2 to 4 is made by the previously described process steps, concurrently with the CO-rich gas stream (or preferably substantially pure carbon monoxide). Crude methanol is then prepared in the manner previously described and purified. Although unpurified methanol and the CO-rich gas stream may be reacted to produce crude acetic acid, it is preferable to react purified methanol with substantially pure carbon monoxide in order to increase the reaction rate and to improve the selectivity.

Theoretically, one mole of carbon monoxide per mole of methanol is necessary to produce one mole of acetic acid, as shown in Equation IV below. The reaction is mildly exothermic; and, in practice, excess carbon monoxide is required, i.e. about 22%.

$$CH_3OH + CO \rightarrow CH_3COOH \qquad \qquad IV$$

Catalysts are commercially available for carbonylation reactions to produce acetic acid at high or low pressure, by either liquid- or vapor-phase reaction.

High-pressure carbonylation reactions for the preparation of crude acetic acid may take place at a temperature in the range of about 338° to 608° F., such as 392°–482° F. and at a pressure in the range of about 15 to 700 atmospheres, such as 150 to 315 atmospheres.

Suitable commercially-available high-temperature carbonylation catalysts for the preparation of acetic acid often comprise two main compounds. One component is a carbonyl-forming metal of the iron group, i.e. Fe, Co, or Ni in the form of a salt i.e. acetate. The other component is a halogen i.e. I, Br, or Cl as a free halogen or a halogen compound. For example, CoI or a mixture of cobalt acetate with an iodine compound are suitable catalysts. A contact time of about 2-3 minutes may be required to obtain 50-65% convesion of methanol by vapor-phase reaction at high pressure. Liquid phase reaction at about 356° F at 258 atm. may take about 3 hrs., for about 51% conversion. Water is used as a solvent or diluent, and it increases the methanol conversion while suppressing the production of methyl acetate. For example, about 30-40 wt. % of water may be present in the reaction zone.

Carbonylation reactions, for the preparation of crude acetic acid by reacting together methanol and carbon monoxide-rich gas or preferably substantially pure CO, may take place at a temperature in the range of about 302° to 392° F. and at a pressure in the range of about 34 to 680 atm., for liquid phase. For 50% conversion of the methanol, the reaction time is about 40-200 minutes. A temperature in the range of about 392° to 572° F. and a pressure in the range of about 1 to 10 atm. may be used for vapor-phase reaction.

Suitable commercially available low-temperature carbonylation catalysts for the prepartion of acetic acid comprise the following combination of ingredients: (1) noble metal catalyst, (2) catalyst promotor, and (3) dispersant or carrier. The noble metal active catalyst may be selected from the group consisting of rhodium, palladium, platinum, iridium, osmium, or ruthenium, in the form of an oxide, organometallic compound, salt, or a coordination compound, consisting of one of said noble metals, CO, a halide, such as chloride, bromide, or iodide, and a suitable amine, organo phosphine, organoarsine, or organostibine ligand. The catalyst promotor may consist of a halogen or halogen compound. The dispersant in liquid-phase processes is a solvent for the metal catalytic component i.e. mixture of acetic acid and water. In vapor-phase processes the same noble-metal compound and promoter as previously described are dispersed on a carrier, i.e. pumice, alumina, activated carbon, or silica.

For example, a typical low-pressure catalyst for the liquid-phase process may comprise $10^{-2}$ to $10^{-4}$ mol/liter of chlorocarbonyl-bis-triphenolphosphine rhodium, and $10^{-4}$ to 2 mol/liter of methyl iodide dissolved in a mixture of acetic acid and water. The ratio of atoms of halogen in the promoter to atoms of noble metal in the catalyst is preferably in the range of about 3 to 300.

In the low-pressure process for the production of glacial acetic acid by liquid-phase carbonylation, at least a portion of the pure methanol as produced previously is mixed in a reactor surge tank with recovered recycled unreacted methanol, catalyst, catalyst promoter, acetic acid solvent for the catalyst, methyl acetate, and water. The mixture is then pumped into a carbonylation reactor, along with substantialy pure carbon monoxide, in which the carbonylation reaction takes place at a temperature, for example of 392° F. and at a pressure of about 35 atmospheres. The gaseous product is cooled and sent to a separation zone in which uncondensed gases and condensate are separated. The uncondensed gas may be scrubbed with fresn methanol to recover the entrained methanol, methyl acetate, and methyl iodide for recycle to the reactor surge tank. Optionally, the residual off-gas may be recycled to the gas generator, or to the water-gas shift converter, or vented. The liquid product from the reactor and the condensate are sent to a separation zone, i.e. distillation zone, in which at a pressure of about 1-3 atm. the low-boiling constituents, such as methanol, methyl acetate, and methyl iodide, are separated and recycled to the reactor surge tank, along with recovered rhodium compound catalyst dissolved in acetic acid, and with water which may be recovered by azeotropically dehydrating acetic acid. Glacial acetic acid product is also separated along with a bottoms stream comprising propionic acid and heavy ends.

Advantageously, the waste bottoms stream of propionic acid and heavy ends, as well as any off-gas stream that is not purged may be recycled to the gas generator as a portion of the feed. By this means the environment is not polluted. Preferably, the pressure in the acetic-acid synthesis zone is the same as that in the partial oxidation gas generator less ordinary pressure drop in the intervening lines and equipment.

DESCRIPTION OF THE DRAWING

Figure 1A:
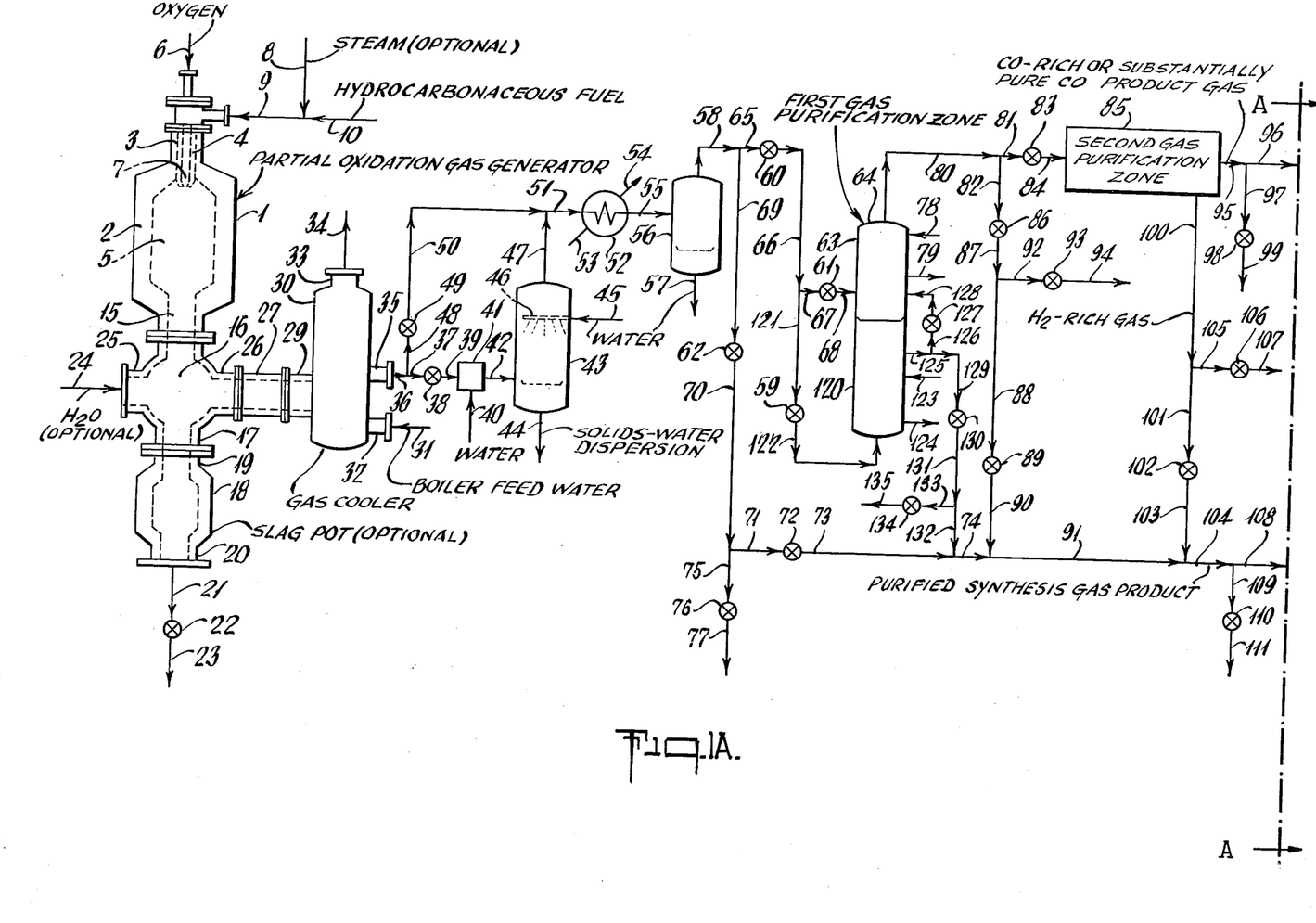
FIG. 1A is a schematic representation of a preferred embodiment of the process for simultaneously making a product stream of clean and purified synthesis gas having a mole ratio $H_2/CO$ in the range of about 2 to 12, and a separate product stream of CO-rich gas and preferably substantially pure CO.
Figure 1B:
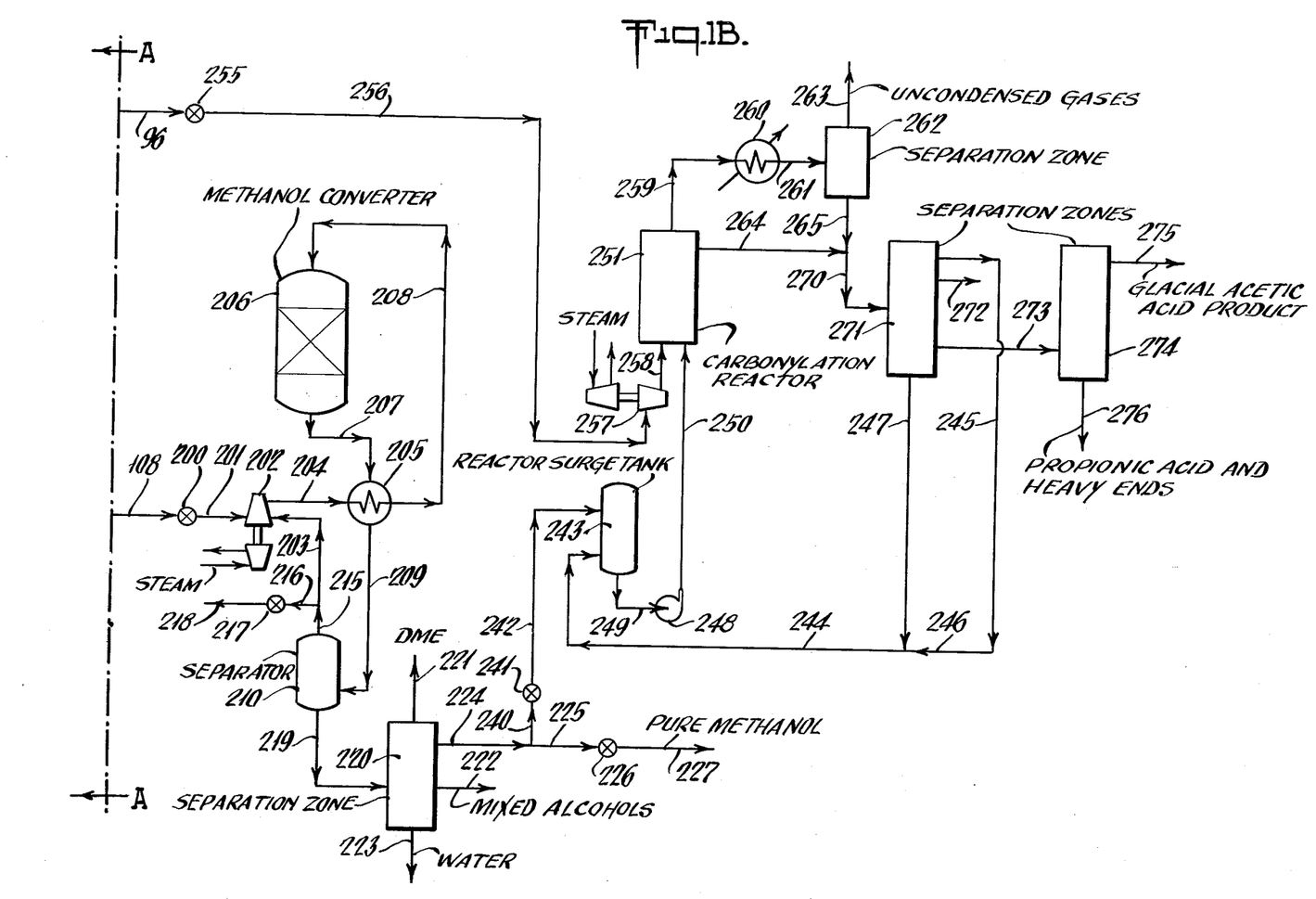

A more complete understanding of the invention may be had by reference to the accompanying schematic drawing. A preferred emodiment of the process of this invention is illustrated by that portion of the drawing, FIG. IA, to the left of line A—A. Other embodiments are shown in FIG. IB to the right of line A—A. It is not intended to limit the continuous process illustrated to the particular apparatus and materials described.

With reference to the FIG. IA, unpacked, free-flow noncatalytic partial oxidation synthesis gas generator 1, as previously described has a refractory lining 2 and an annulus-type burner 3 mounted in its upper inlet port 4 along the vertical axis. The feed streams are introduced into the reaction zone 5 of the gas generator by way of burner 3. They include an oxygen stream which passes through line 6, and the central conduit 7 of the burner, a stream of steam which passes through lines 8 and 9, and a stream of hydrocarbonaceous fuel which passes through lines 10 and 9. The latter two streams are mixed together in line 9 and the mixture is then passed through the annulus passage 4 in burner 3.

The effluent stream of raw synthesis gas leaves the reaction zone and passes through exit passage 15 and directly into a spherically shaped insulated chamber 16. A portion of any entrained solids may drop out of the gas stream and pass through bottom outlet 17 and into slag pot 18 by way of upper inlet 19. The solid material which collects in slag pot 18 is periodically removed through bottom outlet 20, line 21, valve 22, and line 23, or by a lock-hopper system hot shown. When the process gas stream contains little or no entrained solids such as the case with gaseous and some liquid fuels, slag pot 18 may be deleted. Optionally, steam in line 24 may be passed through inlet 25 and injected into the stream of synthesis gas in chanber 16. By this means, the $H_2/CO$ mole ratio of the process gas stream may be increased by the thermal noncatalytic water-gas shift reaction.

The stream of synthesis gas is passed through outlet 26 of chamber 16, insulated line 27 and then through inlet 29 of gas cooler 30 where it is cooled by indirect heat exchange with a stream of boiler feed water from line 31. The boiler feed water passes through inlet 32 and leaves as steam through outlet 33 and line 34. The cooled synthesis gas leaves through outlet 35, lines 36, 37, valve 38, line 39 and is contacted with water from line 40 in orifice or venturi scrubber 41. Any remaining entrained solids i.e. particulate carbon and ash are thereby scrubbed from the raw synthesis gas and pass with the water through line 42 into separation vessel 43. A mixture of solid particles and water is removed through line 44 near the bottom of vessel 43 and is sent to a separator (not shown) where clarified water is separated and recycled to lines 40 and 45. Additional gas scrubbing may be achieved, for example, by passing the stream of synthesis gas through water spray 46 prior to leaving vessel 43 through line 47. When no gas scrubbing is required then all or a portion of the process gas stream in line 36 may be by-passed through line 48, valve 49 and line 50.

The synthesis gas in line 51 is cooled below the dew point in heat exchanger 52 by indirect heat exchange with cold water entering through line 53 and leaving by line 54. The cooled stream passes through line 55 into separation vessel 56 where the condensed water is removed at the bottom by way of line 57 and the gas stream leaves through line 58 at the top.

In the embodiment is the process in which the soot-free dehumidified synthesis gas stream in line 58 contains less than 5PPM of $H_2S$ and COS, valve 59 is closed, valves 60 and 61 are opened, and valve 62 may be opened or closed to permit at least a portion of the gas in line 58 to pass into the $CO_2$-absorption section 63 of first gas purification zone 64 by way of line 65, valve 60, lines 66, 67, valve 61, and line 68. Optionally, a portion of the soot-free dehumidified gas in line 58 by-passes first gas purification zone 64 and second gas purification zone 85, by way of line 69, valve 62, lines 70, 71, valve 72, and lines 73, 74, and 91. Optionally, a portion of the soot-free dehumidified gas stream in line 70 may be removed from the system through line 75, valve 76, and line 77. Lean liquid solvent absorbent enters $CO_2$-absorption zone 63 through line 78 and passes down the column over trays or packing thereby coming in direct contact with the gas stream passing up the column. Rich solvent absorbent leaves section 63 saturated with $CO_2$ through line 79 and goes to a regeneration zone (not shown). The synthesis gas stream containing substantially no $CO_2$ or a controlled amount leaves section 63 through line 80.

The partially purified synthesis gas stream leaving the first gas purification zone by way of line 80 may be then split into two streams 81 and 82. At least a portion of the stream of synthesis gas in line 80 is passed through line 81, valve 83, line 84, and is then subjected to further treatment in a second gas purification zone 85. The remainder of the gas stream if any comprising about 0 to 90 vol. %, such as about 10 to 90 vol. % of the gas stream from line 80 is passed through line 82, valve 86, lines 87–88, valve 89, line 90 and may be mixed in line 91 with the soot-free dehumidified stream of synthesis gas which by-passes the first gas purification zone, if any, from line 74. Optionally, a portion i.e. 0 to 50 vol. % of the partially purified synthesis gas in line 87 may be removed from the system through line 92, valve 93, and line 94.

At least a portion and preferably all of the CO-rich gas or substantially pure carbon monoxide product gas which exits the second gas purification zone 85 through line 95 and 96 may be used in organic synthesis. The remainder may be exported through line 97, valve 98, and line 99. A stream of $H_2$-rich gas leaves CO-separation zone 85 by way of lines 100, 101, valve 102, and line 103. In line 104 at least a portion of the $H_2$-rich gas stream from line 103 is mixed with all of the stream of synthesis gas from line 91. Thus the purified synthesis gas product stream having an increased and controlled $H_2/CO$ mole ratio in line 104 is made by mixing together at least a portion of the $H_2$-rich gas stream from line 103 with at least a portion of one or both of the following streams: (a) soot-free dehumidified synthesis gas which by-passes first and second gas purification zones 64 and 85 in line 91 by way of lines 69, 70, 71, 73, 74, and 91. (b) soot-free dehumidified synthesis gas with at least a portion of the $CO_2$ removed from line 80 that by-passes the second gas purification zone 85 by way of lines 82, 87, 88, 90, and 91.

Any remaining $H_2$-rich gas from line 100 may be exported through line 105 valve 106 and line 107. The synthesis gas product stream in line 104 has a $H_2/CO$ mole ratio in the range of about 2 to 12. At least a portion and preferably all of this gas stream may be passed through line 108 for use in organic synthesis. Any remaining portion of the synthesis gas product stream from line 104 may be passed through line 109, valve 110, and line 111 to export, or recycle to the gas generator either alone or in admixture with other recycle streams.

In another embodiment in which the soot-free dehumidified gas stream in line 58 comprises more than 5 PPM, a desulfurization section 120 is added to the bottom of the first gas purification zone 64. In such case with valves 61 and 62 closed and valves 59 and 60 open, all of the soot-free dehumidified synthesis gas in line 58 is passed into first gas purification zone 64, and none of this gas stream is by-passed around the first gas purification zone by way of line 69, valve 62, line 70 etc. Thus the soot-free dehumidified gas in line 58 is passed through line 65, valve 60, lines 66, 121, valve 59, line 122, into the first stage i.e. lower desulfurization section 120 containing trays or packing where it passes up through the absorption column in direct contact with a stream of liquid solvent absorbent flowing down the column. Lean solvent absorbent in line 123 enters section 120, absorbs $H_2S$ and COS from the synthesis gas, and leaves as rich liquid solvent absorbent by way of line 124. The rich solvent absorbent passes into a regenerator (not shown) to produce lean liquid solvent absorbent which is recycled to section 120 by way of line 123. Desulfurized synthesis gas leaves through line 125 and optionally may be split into two streams. At least a portion of the desulfurized synthesis gas may be passed through line 126, valve 127, and line 128 into upper section 63 of the first gas purification zone where at least a portion of the $CO_2$ in the gas stream is removed in the manner previously described. The remainder of the desulfurized gas stream if any, in line 125 is passed through line 129, valve 130, and lines 131, 132, 74 and 91. Optionally, a portion of this desulfurized gas stream is removed from the system through line 133, valve 134, and line 135.

A desulfurized synthesis gas stream with at least a portion of the $CO_2$ removed leaves the first gas purification zone through line 80. At least a portion of this stream passes into the second gas purification zone by way of line 81, valve 83, and line 84. The remainder of gas stream 80 if any, by-passes the second gas purification zone by way of line 82, valve 86, lines 87, 88, valve 89, and lines 90 and 91. Optionally, a portion of this by-pass stream may be exported through line 92. A CO-rich or substantially pure CO product stream is removed through line 95 of the second gas purification zone, and a $H_2$-rich gas stream is removed through lines 100, 101, valve 102, and line 103. A product stream of purified synthesis gas having a controlled and increased $H_2/CO$ mole ratio in the range of about 2 to 12 is produced by mixing in line 104 at least a portion of the $H_2$-rich gas stream produced in the second gas purification zone in line 103 with at least a portion of one or both of the following: (a) desulfurized synthesis gas produced in the first stage 120 of first gas purification zone 64 and which by-passes the second stage 63 and the second purification zone 85 by way of lines 125, 129, valve 130, lines 131, 132, 74, and 91; (b) desulfurized synthesis gas with at least a portion of the $CO_2$ removed produced in the second stage 63 of first gas purification zone 64 and which by-passes the second purification zone 85 by way of lines 80, 82, valve 86, lines 87, 88, valve 89, and lines 90 and 91.

In another embodiment shown in FIG. 1B, pure methanol is made by the catalytic reaction of at least a portion of cleaned and purified product stream of methanol synthesis gas from line 108. The process steps are shown to the right of section line A—A in the drawing. The process gas stream from line 108 is passed through valve 200, and line 201 into steam turbocompressor-circulator 202 along with unconverted recycle gases from line 203. The compressed gases in line 204 are then preheated in heat exchanger 205 by indirect heat exchange with the hot impure methanol vapor leaving catalytic methanol reactor 206 by way of line 207. The preheated methanol synthesis gas stream in line 208 is passed through methanol reactor 206 where reactions between $H_2$ and carbonic oxides take place to produce crude methanol. After being partially cooled in heat exchanger 205, the methanol reaction products pass through line 209 into separation zone 210 where the unreacted gases are separated from the crude methanol. The unreacted gases are passed through lines 215 and 203 into recycle compressor 202, except for the purge gas which is passed through line 216, valve 217, and line 218. The crude methanol in line 219 is introduced into the purification zone 220 where impurities are removed, for example, by distillation. Dimethyl ether may be removed through line 221, mixed alcohols through line 222, and water through line 223. Pure methanol may be drawn off through lines 224, 225, valve 226, and line 227. Optionally, by-product oxygen-containing organic compounds from lines 221, 222, and 218 may be recycled to the gas generator as a portion of the fuel and to reduce the free-oxygen requirements for a given level of soot production.

In still another embodiment of the invention a raw stream of acetic acid is prepared by the low pressure liquid-phase catalytic carbonylation reaction between the pure methanol and the substantially pure carbon monoxide made previously in the subject process. In such case, at least a portion of the pure methanol in line 224 is passed through line 240, valve 241, and line 242 into reactor surge tank 243 and mixed with a mixture of recycle materials from line 244. Recycle stream 244 comprises a mixture of methanol, methyl acetate, and methyl iodide from lines 245 and 246 and a rhodium catalyst compound i.e. $Rh(CO)[P(C_6H_5)_3]_2Cl$ dissolved in a mixture of acetic acid and water from line 247.

By means of pump 248, the reactant mixture in tank 243 is pumped through lines 249 and 250 into vertical carbonylation reactor 251. Simultaneously, at least a portion of the substantially pure CO gas stream in line 96 is passed into carbonylation reactor 251 by way of valve 255, line 256, optionally steam turbocompressor 257, and line 258. In reactor 251, methanol and CO react to produce acetic acid. An overhead gaseous stream is passed through line 259, cooled in heat exchanger 260, and passed through line 261 into separator 262. The uncondensed gases in line 263 are scrubbed with fresh methanol in a tower (not shown) to recover entrained methanol, methyl acetate and methyl iodide for recycle to the reactor surge tank 243. Residual off-gas from the scrubber may be recycled to the gas generator or vented.

The liquid product from the reactor in line 264 and the condensate from line 265 are passed through line 270 into separation zone 271. For example, by distillation, the low boiling constituents comprising a mixture of methanol, methyl acetate, and methyl iodide may be separated and leave by way of line 245; water is removed through line 272; recovered rhodium compound catalyst dissolved in acetic acid is removed through line 247; and impure acetic acid is removed through line 273 and fed into separation zone 274. Glacial acetic acid is recovered as a distillate from line 275. Propionic acid and heavier components leave through line 276 and may be recycled to the gas generator as a portion of the fuel.

EXAMPLE

The following example illustrates an embodiment of the process of this invention for simultaneously and continuously producing a stream of methanol synthesis gas and a stream of substantially pure carbon monoxide. The example should not be construed as limiting the scope of the invention. Reference is made to the drawing.

The feed to a noncatalytic free-flow partial-oxidation gas generator comprises 20.99 million standard cubic feet per day of natural gas and 13.94 million standard cubic feet per day of substantially pure oxygen (99 mole % $O_2$). The composition of the natural gas follows: $CH_4$ 87.62, $C_2H_6$ 7.96, $C_3H_8$ 0.61, $CO_2$ 1.25 and $N_2$ 2.56. No $H_2O$ is introduced into the gas generator.

65.01 Million standard cubic feet per day of raw synthesis gas leave the reaction zone of the gas generator at a temperature of 2600° F and a pressure of 896.0 psig. The amount in million standard cubic feet per day (MMSCF/day) and composition in mole % of the raw synthesis gas stream leaving the reaction zone at reference number 15 in the drawing is shown in column 1 of Table I, which follows. Because no solids are entrained in the gas stream leaving the gas generator, slag pot 18 and the carbon-scrubbing zone comprising 41 and 43 in FIG. 1A may be deleted. Further, no water-gas shifting is required in the subject process to increase the $H_2/CO$ mole ratio.

The amount and composition of the dehumidified gas stream leaving gas-liquid separator 56 by way of line 58 is shown in column 2 of Table I. The gas stream in line 58 is then divided into two streams. One stream in line 69 by-passes the first gas purification zone 64. The other stream in line 65 is introduced into the first gas purification zone. The amounts and compositions of gas streams 69 and 65 are shown respectively in columns 3 and 4 of the foregoing that various modifications of the process and materials disclosed herein can be made without departure from the spirit of the invention.

TABLE I

GAS COMPOSITION

| Column No. | 1 | | 2 | | 3 | | 4 | |
|---|---|---|---|---|---|---|---|---|
| Drawing Reference No. | 15 | | 58 | | 69 | | 65 | |
| | MMSCF/day | Mole % | MMSCF/day | Mole % | MMSCF/day | Mole % | MMSCF/day | Mole % |
| CO | 21.118 | 32.48 | 21.118 | 35.13 | 15.204 | 35.13 | 5.914 | 35.13 |
| $H_2$ | 37.123 | 57.10 | 37.123 | 61.76 | 26.726 | 61.76 | 10.397 | 61.76 |
| $CO_2$ | 1.119 | 1.72 | 1.119 | 1.86 | 0.806 | 1.86 | 0.313 | 1.86 |
| $H_2O$ | 4.900 | 7.54 | — | — | — | — | — | — |
| $CH_4$ | 0.143 | 0.22 | 0.143 | 0.24 | 0.103 | 0.24 | 0.040 | 0.24 |
| $A_r$ | 0.069 | 0.11 | 0.069 | 0.12 | 0.050 | 0.12 | 0.019 | 0.12 |
| $N_2$ | 0.537 | 0.83 | 0.537 | 0.73 | 0.387 | 0.89 | 0.150 | 0.89 |
| $H_2S$ | — | — | — | — | — | — | — | — |
| COS | — | — | — | — | — | — | — | — |
| Wet Total | 65.009 | 100.00 | — | — | — | — | — | — |
| Dry Total | 60.109 | 100.00 | 60.109 | 100.00 | 43.276 | 100.00 | 16.833 | 100.00 |
| ($H_2$+CO) | 58.241 | 89.58 | 58.241 | 96.89 | 41.930 | 96.89 | 16.311 | 96.89 |

| Column No. | 5 | | 6 | | 7 | | 8 | | 9 | |
|---|---|---|---|---|---|---|---|---|---|---|
| Drawing Reference No. | | | 80 | | 96 | | 100 | | 108 | |
| | MMSCF/day | Mole % | MMSCF/day | Mole % | MMSCF/day | Mole % | MMSCF/day | Mole % | MMSCF/day | Mole % |
| CO | 0.093 | 20.35 | 5.821 | 35.55 | 4.981 | 96.16 | 0.840 | 7.50 | 16.044 | 29.45 |
| $H_2$ | 0.047 | 10.28 | 10.350 | 63.19 | 0.025 | 0.48 | 10.325 | 92.22 | 37.051 | 68.02 |
| $CO_2$ | 0.313 | 68.49 | — | — | — | — | — | — | 0.806 | 1.48 |
| $H_2O$ | 0.0 | 0.0 | — | — | — | — | — | — | — | — |
| $CH_4$ | 0.003 | 0.66 | 0.037 | 0.23 | 0.037 | 0.71 | — | — | 0.103 | 0.19 |
| $A_r$ | 0.0 | 0.0 | 0.019 | 0.12 | 0.017 | 0.33 | 0.002 | 0.02 | 0.052 | 0.10 |
| $N_2$ | 0.0 | 0.0 | 0.149 | 0.91 | 0.120 | 2.32 | 0.029 | 0.26 | 0.416 | 0.76 |
| $H_2S$ | 0.0 | 0.0 | — | — | — | — | — | — | — | — |
| COS | 0.0 | 0.0 | — | — | — | — | — | — | — | — |
| Wet Total | — | — | — | — | — | — | — | — | — | — |
| Dry total | 0.457 | 100.00 | 16.376 | 100.00 | 5.180 | 100.00 | 11.196 | 100.00 | 54.472 | 100.00 |
| ($H_2$+CO) | 0.140 | 30.63 | 16.171 | 98.74 | 5.006 | 96.64 | 11.165 | 99.72 | 53.095 | 27.47 |

Table I. Substantially all of the $CO_2$ is separated in the first gas-purification zone. The amount and composition of the $CO_2$ tail gas recovered in a solvent regenerator 35 (not shown) is shown in column 5 of Table I.

The purified synthesis gas stream leaving the first gas-purification zone through line 80 is shown in column 6 of Table I. All of this gas stream is introduced into the second gas-purification zone, in which it is separated into the CO-rich product gas stream in line 96 and the $H_2$-rich gas stream in line 100. The amounts and compositions of these gas streams are shown, respectively, in columns 7 and 8 of Table I.

The product gas of methanol-synthesis gas is then produced by mixing together in line 104 all of the soot-free dehumidified gas stream that by-passes the first gas purification zone by way of line 69, valve 62, lines 70, 71, valve 72, and lines 73, 74, and 91 with all of the $H_2$-rich gas stream from lines 100, 101, valve 102 and line 103. The amount and composition of this methanol-synthesis product gas stream in line 108 is shown in column 9 of Table I. This is the proper gas composition for mixing with unconverted recycle gas from a catalytic methanol converter to produce a feed gas for converting into crude methanol. Pure methanol may be produced by distillation and reacted in a catalytic carbonylation reactor with at least a portion of the stream of substantially pure carbon monoxide from stream 96 to produce crude acetic acid in the manner described previously in connection with FIG. 1B of the drawing. Glacial acetic acid may be then produced by purification.

The process of the invention has been described generally and by examples, with reference to a hydrocarbonaceous fuel, synthesis gas, and $H_2$-rich gas of particular compositions, for purposes of clarity and illustration only. It will be apparent to those skilled in the art from the foregoing that various modifications of the process and materials disclosed herein can be made without departure from the spirit of the invention.

I claim:

1. Process for simultaneous production of a product stream of purified synthesis gas and a product stream of CO-rich gas, comprising:
   (1) reacting a hydrocarbonaceous feedstock with a free-oxygen-containing gas, optionally in the presence of a temperature moderator, in the reaction zone of a free-flow noncatalytic partial-oxidation gas generator at a temperature in the range of about 1300° to 3000° F and at a pressure in the range of about 1 to 250 atmospheres to produce an effluent gas stream comprising $H_2$, CO, $H_2O$, $CO_2$, and optionally at least one material from the group $H_2S$, COS, $CH_4$, $N_2$, $A_r$, and solid particles;
   (2) removing a portion of said solid particles if present, cooling the effluent gas stream by indirect heat exchange in a separate heat-exchange zone, removing any remaining entrained solid particles, and dehumidifying the cooled gas stream;
   (3) introducing at least a portion of the clean dehumidified gas stream from (2) into a first gas-purification zone and by-passing said first gas-purification zone with the remainder if any; removing from the gas stream in said first gas-purification zone any $H_2S$, COS, and at least a portion of the $CO_2$;
   (4) introducing partially purified gas from the first gas purification zone in (3) into a second gas-purification zone and by-passing said second gas-purification zone with at least a portion of the remainder, if any, and removing from said second gas-purification zone said product stream of CO-rich gas and a separate stream of $H_2$-rich gas; and (5) mixing together at least a portion of the $H_2$-rich gas from (4) with at least a portion of at least one of the following:
  (a) gas processed in the first gas purification zone that by-passes the second gas purification zone in (4);
  (b) soot-free dehumidified gas that by-passes the first gas-purification zone in (3); producing said product stream of purified synthesis gas having a controlled $H_2/CO$ mole ratio.

2. The process of claim 1 in which the effluent gas stream from the reaction zone in step (1) and the synthesis gas from the first-gas purification zone in step (3) have a mole ratio $H_2/CO$ in the range of about 0.5 to 1.9, and the product stream of purified synthesis gas from step (5) has a mole ratio $H_2/CO$ in the range of about 2 to 12.

3. The process of claim 2 in which said product stream of purified synthesis gas is methanol synthesis gas having a $H_2/CO$ mole ratio in the range of about 2–4.

4. The process of claim 1 in which said product stream of purified synthesis gas is delivered at a pressure which is about that in the synthesis gas generator less ordinary drop in the intervening lines and equipment.

5. The process of claim 1 in which the following gas streams contain substantially no water: (a) the acid-gas free synthesis gas from step (3), (b) the $H_2$-rich gas stream from step (4), and (c) the CO-rich product gas stream from step (4).

6. The process of claim 1 in which said product stream of CO-rich gas from step (4) is substantially pure CO containing about 90–99.5 mole percent CO.

7. The process of claim 1 in which from about 10 to 100 volume % of the clean dehumidified gas stream from step (2) is introduced into said first gas-purification zone in step (3).

8. The process of claim 1 in which about 10 to 90 vol. % of the synthesis gas leaving the first gas-purification zone in step (3) is introduced into the second gas-purification zone in step (4), and the remainder of said synthesis gas comprising about 90 to 10 vol. % by-passes the second gas-purification zone in step (4) and is mixed with said gases in step (5) to produce said stream of product gas.

9. The process of claim 1 provided with the additional step of introducing supplemental steam into the effluent gas stream from (1) in the amount of about 0.1 to 2.5 moles of supplemental steam per mole of effluent gas stream, and, in a separate free-flow unpacked reaction zone at a pressure substantially that in said synthesis-gas generator, less ordinary line drop, and at a temperature of at least 1500° F reacting together $H_2O$ and a portion of the CO in the effluent gas from (1) so as to increase the mole ratio ($H_2/CO$).

10. The process of claim 1 in which said free-oxygen-containing gas is substantially pure oxygen (95 mole percent $O_2$ or more).

11. The process of claim 1 in which said hydrocarbonaceous feedstock is selected from the group consisting of liquefied petroleum gas, liquefied natural gas, petroleum distillates and residue, naphtha, gas oil, residual fuel, reduced crude, whole crude, asphalt, coal tar, coal-derived oil, shale oil, tarsand oil, and pumpable slurries of coal, particulate carbon, and petroleum coal in water or in liquid hydrocarbon fuel, and mixtures thereof.

12. The process of claim 1 in which said hydrocarbonaceous feedstock is selected from the group consisting of methane, ethane, butane and other unsaturated light hydrocarbon gases, natural gas, water-gas, coke-oven gas, synthesis gas, refinery gas, and mixtures thereof.

13. The process of claim 1 in which said hydrocarbonaceous feedstocks are organic materials selected from the group consisting of carbohydrates, cellulosic materials, aldehydes, organic acids, alcohols, ketones, oxygenated fuel oil, waste liquids, and by-products from chemical processes containing oxygenated hydrocarbonaceous organic materials, and mixtures thereof.

14. The process of claim 1 in which a portion of the $CO_2$ from the first gas purification zone is recycled to the gas generator.

15. The process of claim 1 in which the partially purified gas from the first gas purification zone is contacted with a sulfur-free liquefied $CH_4$-rich gas stream in a separation column in said second gas-purification zone; and with the step of passing the bottoms stream from said separation column into the partial oxidation gas generation operation in step (1) as at least a portion of the feed.

16. The process of claim 1 in which said product stream of purified synthesis gas is methanol synthesis gas having an $H_2/CO$ mole ratio in the range of about 2–4, said product stream of CO-rich gas from step (4) is substantially pure CO, and provided with the additional steps of reacting at least a portion of said methanol synthesis gas in the presence of a methanol catalyst in a methanol-synthesis zone at a temperature in the range of about 400° to 750° F and at a pressure in the range of about 40 to 350 atm. to produce crude methanol, and purifying said crude methanol to produce substantially pure methanol and by-product oxygen-containing organic materials.

17. The process of claim 16 in which said methanol catalyst comprises zinc oxide and chromium oxide, the temperature in said methanol-synthesis zone is in the range of about 650° to 750° F, and the pressure is in the range of about 250 to 350 atm.

18. The process of claim 16 in which said methanol catalyst comprises copper oxide, zinc oxide, chromium oxide, or aluminum oxide, the temperature in said methanol-synthesis zone is in the range of about 400° to 660° F, and the pressure is in the range of about 40 to 250 atm.

19. The process of claim 16 in which the pressure in said methanol-synthesis zone is the same as that in the synthesis-gas generator less ordinary pressure drop in the intervening lines and equipment.

20. The process of claim 16 in which at least a portion of said by-product oxygen-containing organic materials is recycled to the synthesis gas generator as a portion of the hydrocarbonaceous feed.

21. The process of claim 16 in which at least a portion of said substantially pure methanol is used in said first gas-purification zone to absorb gaseous impurities from the gas streams.

22. The process of claim 16 is provided with the additional steps of reacting at least a portion of said substantially pure methanol with at least a portion of said substantially pure carbon monoxide in the presence of a carbonylation catalyst in an acetic-acid-synthesis zone at a temperature in the range of about 302° to 608° F and at a pressure in the range of about 1 to 700 atmospheres to produce impure acetic acid, and purifying said impure acetic acid to produce substantially pure acetic acid and by-product oxygen-containing organic materials.

23. The process of claim 22 in which said carbonylation catalyst comprises a carbonyl-forming metal selected from the group Fe, Co, and Ni, in the form of a salt, and a halogen selected from the group I, Br, Cl, in the form of a free halogen or halogen compound, and the temperature in said acetic-acid-synthesis zone is in the range of about 338° to 608° F, and the pressure is in the range of about 15 to 700 atmospheres.

24. The process of claim 22 in which said carbonylation catalyst comprises in admixture (1) a noble metal from the group rhodium, palladium, platinum, iridium, osmium, and ruthenium, in the form of an oxide, organometallic compound, salt, or coordination compound; (2) a halogen or halogen-compound promoter; and (3) a dispersant selected from the group, acetic acid and water, pumice, alumina, activated carbon, and silica; and the temperature in said acetic-acid-synthesis zone is in the range of about 302° to 392° F, and the pressure is in the range of about 34 to 680 atm. for liquid-phase reaction.

25. The process of claim 22 in which the temperature in said acetic-acid-synthesis zone is in the range of about 392° to 572° F and the pressure is in the range of about 1 to 10 atm. for vapor-phase reaction.

26. The process of claim 22 in which the pressure in said acetic acid synthesis zone is the same as that in said synthesis-gas generator less ordinary pressure drop in the intervening lines and equipment.

27. The process of claim 22 in which at least a portion of said by-product oxygen-containing organic materials is recycled to said synthesis-gas generator as a portion of the hydrocarbonaceous feed.

28. Process for the production of methanol, comprising:
   (1) reacting a substantially sulfur-free hydrocarbonaceous feedstock with substantially pure oxygen, optionally in the presence of a temperature moderator, in the reaction zone of a free-flow noncatalytic partial-oxidation gas generator at a temperature in the range of about 1300° to 3000° F and at a pressure in the range of about 1 to 250 atmospheres to produce an effluent gas stream comprising $H_2$, CO, $H_2O$, $CO_2$ and at least one material from the group consisting of $CH_4$, $N_2$, $A_r$, particulate carbon, and ash;
   (2) cooling the effluent gas stream by indirect heat exchange in a separate heat-exchange zone, removing any entrained particulate carbon and ash, and dehumidifying the cooled gas stream;
   (3) splitting the soot-free dehumidified gas stream from (2) into first and second gas streams with said first split gas stream comprising about 10 to 90 volume percent of the effluent gas stream from (2), and said second split stream comprising the remainder;
   (4) purifying said first split gas stream from (3) in a first gas-purification zone and separating therefrom at least a portion of the $CO_2$;
   (5) splitting the gas stream from (4) into third and fourth gas streams with said third gas stream comprising about 10 to 100 volume percent of said synthesis-gas stream from (4) and said fourth gas stream containing the remainder if any and introducing all of said third gas stream into a second gas-purification zone;
   (6) removing a stream of CO-rich gas and a stream of $H_2$-rich gas from said second gas-purification zone;
   (7) mixing together at least a portion of said second gas stream from (3), at least a portion of said $H_2$-rich gas stream from (6), and at least a portion of said fourth gas stream if any from (5), to produce a stream of methanol-synthesis gas; and
   (8) reacting at least a portion of said methanol synthesis gas in the presence of a methanol catalyst in a methanol-synthesis zone at a temperature in the range of about 400° to 750° F and at a pressure in the range of about 40 to 350 atm. to produce crude methanol, and purifying said crude methanol to produce substantially pure methanol and by-product oxygen-containing organic materials.

29. The process of claim 28, in which the mole ratio, $H_2/(2CO+3CO_2)$, of the methanol-synthesis gas from step (7) is in the approximate range of 1.01 to 1.05.

30. The process of claim 28 in which a portion of said substantially pure methanol is recycled to said first gas-purification zone as a solvent absorbent.

31. The process of claim 28, provided with the additional step of introducing supplemental steam into the effluent gas stream from (1) in the amount of about 0.1 to 2.5 moles of supplemental steam per mole of effluent gas stream and, in a separate free-flow unpacked reaction zone at a pressure substantially that in said synthesis-gas generator, less ordinary line drop, and at a temperature of at least 1500° F, reacting together $H_2O$ and a portion of the CO in the effluent gas stream so as to increase the mole ratio ($H_2$/CO) of the process gas stream.

32. The process of claim 28, in which the CO-rich gas in step (6) is substantially pure CO, and provided with the additional steps of reacting at least a portion of said substantially pure methanol with at least a portion of said substantially pure carbon monoxide in the presence of a carbonylation catalyst in an acetic acid-synthesis zone, at a temperature in the range of about 302° to 608° F and at a pressure in the range of about 1 to 700 atmospheres, to produce impure acetic acid, and purifying said impure acetic acid to produce substantially pure acetic acid and by-product oxygen-containing organic materials.

33. The process of claim 32, in which at least a portion of said by-product oxygen-containing organic materials are recycled to the reaction zone of said gas generator.

34. The process of claim 32, in which at least a portion of said pure acetic acid is recycled to said second gas-purification zone in step (5) to effect CO-separation from said third gas stream.

35. Process for the simultaneous production of a product stream of purified synthesis gas and a product stream of CO-rich gas, comprising:
   (1) reacting a hydrocarbonaceous feedstock with a free-oxygen-containing gas, optionally in the presence of a temperature moderator, in the reaction zone of a free-flow noncatalytic partial-oxidation gas generator at a temperature in the range of about 1300° to 3000° F and at a pressure in the range of about 1 to 250 atmospheres to produce an effluent gas stream comprising $H_2$, CO, $H_2O$, $CO_2$, $H_2S$, COS and optionally at least one material from the group consisting of $CH_4$, $N_2$, $A_r$, and solid particles;
   (2) removing a portion of said solid particles if present, cooling the effluent gas stream by indirect heat exchange in a separate heat-exchange zone, removing any remaining entrained solid particles and dehumidifying the cooled gas stream;

(3) desulfurizing the gas stream from (2) in the first stage of a two-stage first gas purification zone, introducing at least a portion of the desulphurized gas stream from the first stage into the second stage of said first gas purification zone and removing at least a portion of the $CO_2$; and by-passing said second stage with the remainder of said desulfurized gas from the first stage of said first gas purification zone if any;

(4) introducing at least a portion of the gas stream leaving the second stage of said first gas purification zone into a second gas purification zone when there is a stream of desulfurized gas from the first stage that by-passes said second stage, or introducing into said second gas purification zone a portion of the gas stream leaving the second stage of said first gas purification zone when there is no desulfurized gas stream that by-passes said second stage; and by-passing said second gas purification zone with the remainder of said gas stream leaving the second stage of said first gas purification zone if any;

(5) removing from said second gas purification zone, a product stream of CO-rich gas and a stream of $H_2$-rich gas; and (6) mixing together at least a portion of the $H_2$-rich gas stream from (5) with at least a portion of at least one of the following: (a) desulfurized gas stream that by-passes the second stage of the first gas purification zone in (3); (b) desulfurized gas stream with at least a portion of the $CO_2$ removed that leaves the second stage of the first gas purification zone and which by-passes said second gas purification zone in (4); producing said product stream of purified synthesis gas having a controlled $H_2/CO$ mole ratio.

36. Process for the simultaneous production of a product stream of purified synthesis gas and a product stream of CO-rich gas comprising:

(1) reacting a hydrocarbonaceous feedstock with a free-oxygen-containing gas, optionally in the presence of a temperature moderator, in the reaction zone if a free-flow noncatalytic partial-oxidation gas generator at a temperature in the range of about 1300° to 3000° F and at a pressure in the range of about 1 to 250 atmospheres to produce an effluent gas stream comprising $H_2$, CO, $H_2O$, $CO_2$, $H_2S$, COS, and optionally at least one material from the group consisting of $CH_4$, $N_2$, $A_r$, and solid particles;

(2) removing a portion of said solid particles if present, cooling the effluent gas stream by indirect heat exchange in a separate heat-exchange zone, removing any remaining entrained solid particles and dehumidifying the cooled gas stream;

(3) desulphurizing the gas stream from (2) and removing at least a portion of the $CO_2$ by direct contact with a liquid solvent absorbent in a first gas purification zone;

(4) introducing a portion of the process gas stream from (3) into a second gas purification zone, and by-passing said second gas purification zone with the remainder of said desulfurized gas stream with at least a portion of the $CO_2$ removed from (3);

(5) removing from said second gas purification zone a product stream of CO-rich gas and a stream of $H_2$-rich gas; and (6) mixing together to produce said product stream of purified synthesis gas having a controlled $H_2/CO$ mole ratio at least a portion of said $H_2$-rich gas stream with at least a portion of the remainder of the desulfurized gas stream with at least a portion of the $CO_2$ removed that by-passes the second gas purification zone in step (4).

37. Process for simultaneous production of a product stream of purified synthesis gas and a product stream of CO-rich gas, comprising:

(1) reacting a substantially sulfur-free hydrocarbonaceous feedstock with a free-oxygen-containing gas, optionally in the presence of a temperature moderator, in the reaction zone of a free-flow noncatalytic partial-oxidation gas generator at a temperature in the range of about 1300° to 3000° F and at a pressure in the range of about 1 to 250 atmospheres to produce an effluent gas stream comprising $H_2$, CO, $H_2O$, $CO_2$ and optionally at least one material from the group $CH_4$, $N_2$, $A_r$, and solid particles;

(2) cooling the effluent gast stream by indirect heat exchange in a separate heat-exchange zone, removing any entrained solid particles and dehumidifying the cooled gas stream;

(3) introducing at least a portion of the dehumidified gas stream from (2) into a first gas-purification zone, and by-passing said first gas-purification zone with the remainder of said dehumidified gas stream from (2) if any; and removing from the process gas stream in said first gas purification zone at least a portion of the $CO_2$;

(4) introducing at least a portion of the gas stream leaving the first gas purification zone into a second gas purification zone when there is a stream of soot-free dehumidified gas by-passing said first gas purification zone, or introducing a portion of the gas stream leaving the first gas purification zone into the second gas purification zone when there is no stream of soot-free dehumidified gas by-passing said first gas purification zone; and by-passing said second gas purification zone with the remainder of the gas stream leaving the first gas purification zone if any;

(5) removing from said second gas purification zone, a product stream of CO-rich gas and a stream of $H_2$-rich gas; and (6) mixing together at least a portion of the $H_2$-rich gas stream from (5) with at least a portion of at least one of the following: (a) dehumidified gas stream from (2) that by-passes the first gas-purification zone in (3); (b) partially purified synthesis gas leaving the first gas purification zone with at least a portion of the $CO_2$ removed and which by-passes the second gas-purification zone in (3) if any; producing said product stream of purified synthesis gas having a controlled $H_2/CO$ mole ratio.

* * * * *